United States Patent
Davignon et al.

(10) Patent No.: US 9,554,862 B2
(45) Date of Patent: Jan. 31, 2017

(54) MORPHOLOGICALLY CURVED SAGITTAL WALL OF A TIBIAL IMPLANT

(71) Applicant: Mako Surgical Corp., Fort Lauderdale, FL (US)

(72) Inventors: Robert Davignon, Morris Plains, NJ (US); Michael C. Ferko, Warwick, NY (US); Stuart L. Axelson, Jr., Succasunna, NJ (US)

(73) Assignee: Mako Surgical Corp., Fort Lauderdale, FL (US)

( * ) Notice: Subject to any disclaimer, the term of this patent is extended or adjusted under 35 U.S.C. 154(b) by 111 days.

(21) Appl. No.: 14/297,097

(22) Filed: Jun. 5, 2014

(65) Prior Publication Data

US 2015/0351859 A1    Dec. 10, 2015

(51) Int. Cl.
| | |
|---|---|
| *A61F 2/38* | (2006.01) |
| *A61B 19/00* | (2006.01) |
| *G06F 19/00* | (2011.01) |
| *A61F 2/30* | (2006.01) |

(52) U.S. Cl.
CPC ............. *A61B 19/50* (2013.01); *A61B 34/10* (2016.02); *A61F 2/389* (2013.01); *G06F 19/3437* (2013.01); *A61F 2002/30112* (2013.01); *A61F 2002/3895* (2013.01); *A61F 2230/0063* (2013.01)

(58) Field of Classification Search
CPC .......... A61F 2/3094–2002/30963; A61F 2/389
See application file for complete search history.

(56) References Cited

U.S. PATENT DOCUMENTS

| | | | |
|---|---|---|---|
| 2004/0068187 A1* | 4/2004 | Krause | A61B 17/15 600/443 |
| 2009/0228113 A1* | 9/2009 | Lang | A61F 2/30942 623/20.32 |
| 2011/0029091 A1* | 2/2011 | Bojarski | A61F 2/30942 623/20.32 |
| 2011/0087332 A1* | 4/2011 | Bojarski | A61B 17/155 623/20.32 |
| 2011/0264097 A1* | 10/2011 | Hodorek | A61F 2/389 606/88 |
| 2012/0330429 A1 | 12/2012 | Axelson, Jr. et al. | |
| 2013/0166254 A1 | 6/2013 | Grimm et al. | |
| 2013/0312897 A1 | 11/2013 | Vowles | |

* cited by examiner

*Primary Examiner* — Zade Coley
(74) *Attorney, Agent, or Firm* — Lerner, David, Littenberg, Krumholz & Mentlik, LLP

(57) ABSTRACT

Disclosed herein are methods of designing and fabricating prosthetic implants having a sagittal wall in which at least a portion thereof traverses a non-linear path. A method of fabricating such a prosthetic implant may include generating a virtual bone model based on image information obtained from at least one bone, determining a proposed height of the prosthetic implant at a first location on the virtual bone model, determining a proposed resection depth into the at least one bone at the first location based at least in part on the proposed height of the prosthetic implant, and determining a curved resection path across a portion of the virtual bone model. The curved resection path may intersect the first location and the prosthetic implant may have a curved sagittal wall corresponding to the curved resection path.

19 Claims, 14 Drawing Sheets

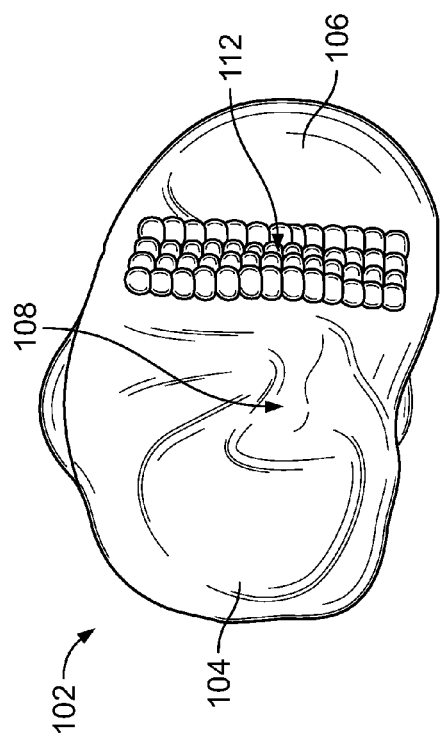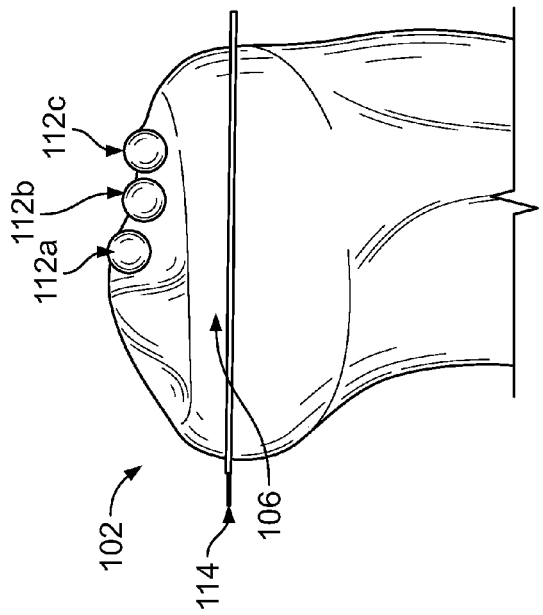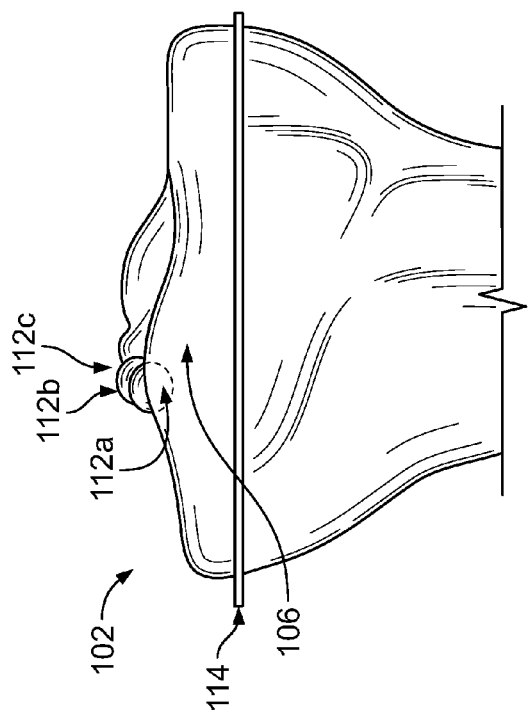

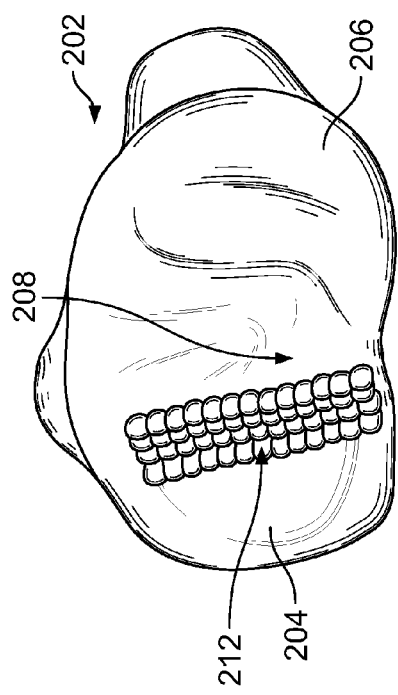
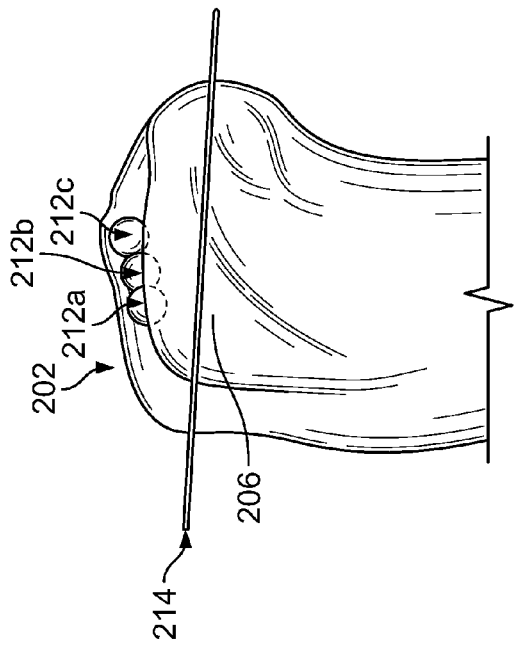
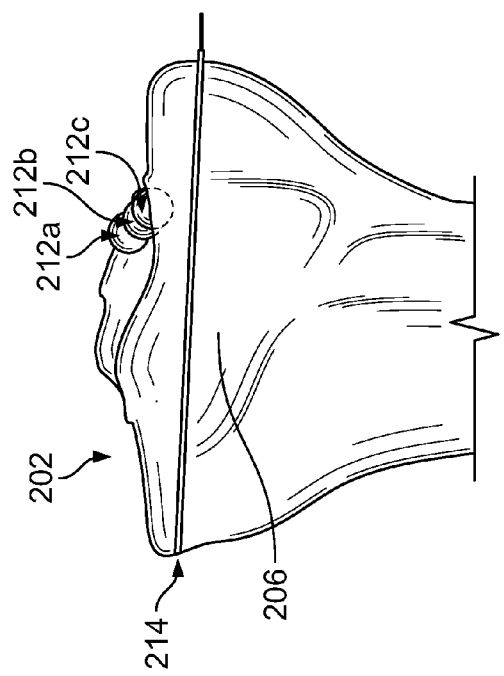

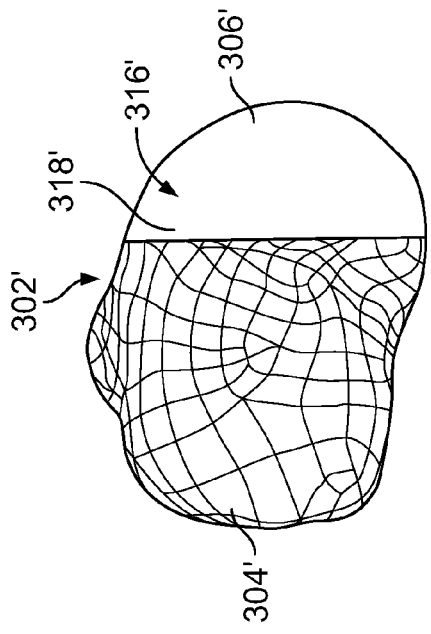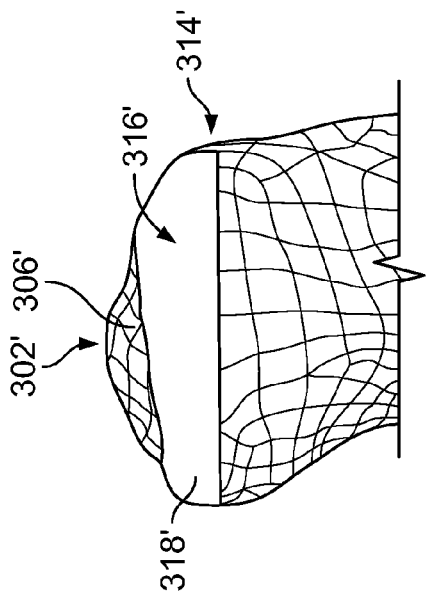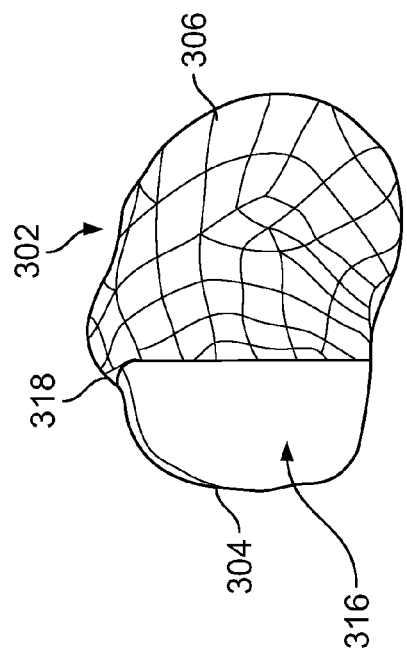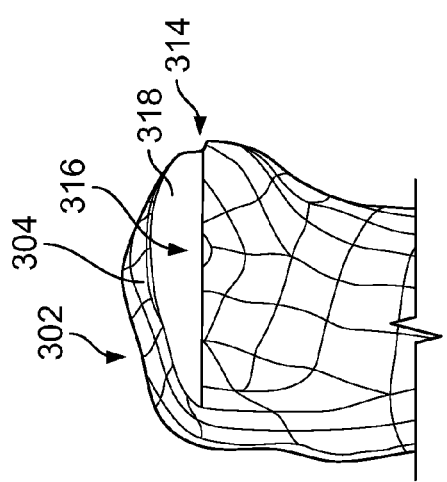

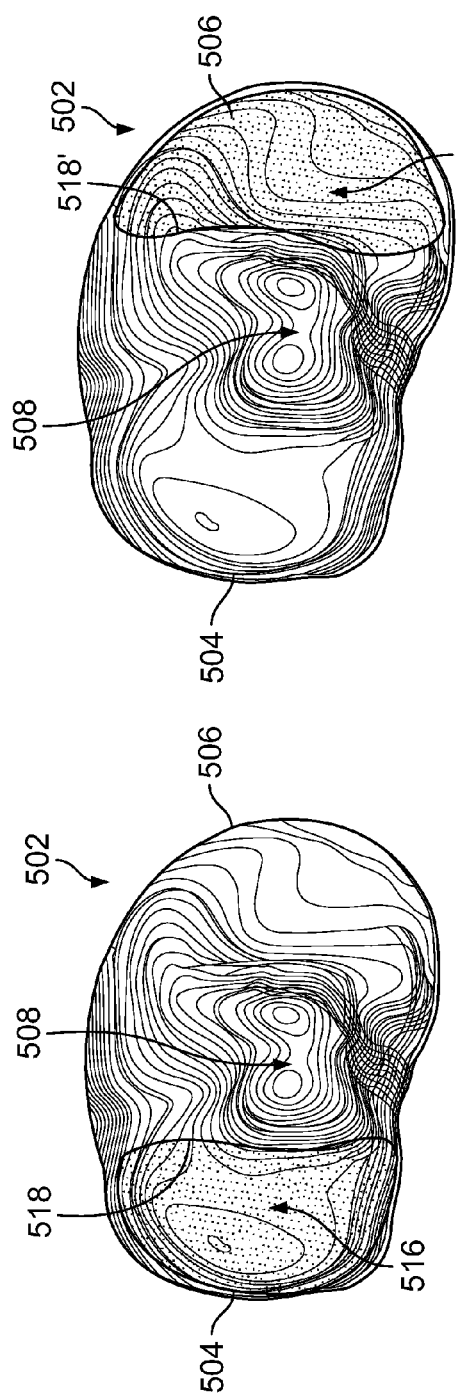
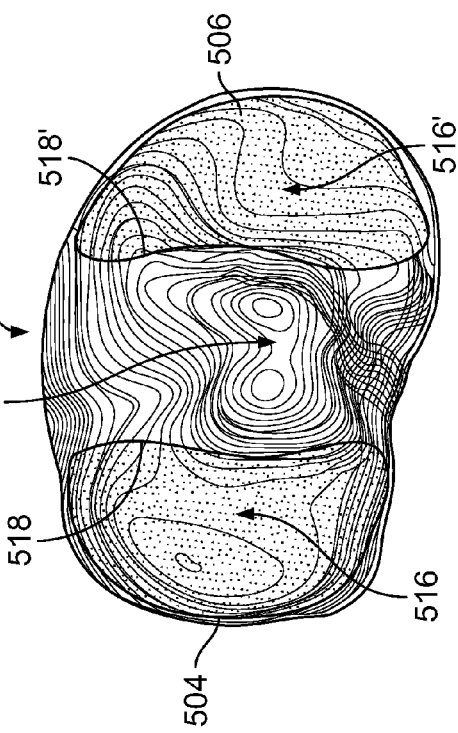
FIG. 9A
FIG. 9B
FIG. 9C

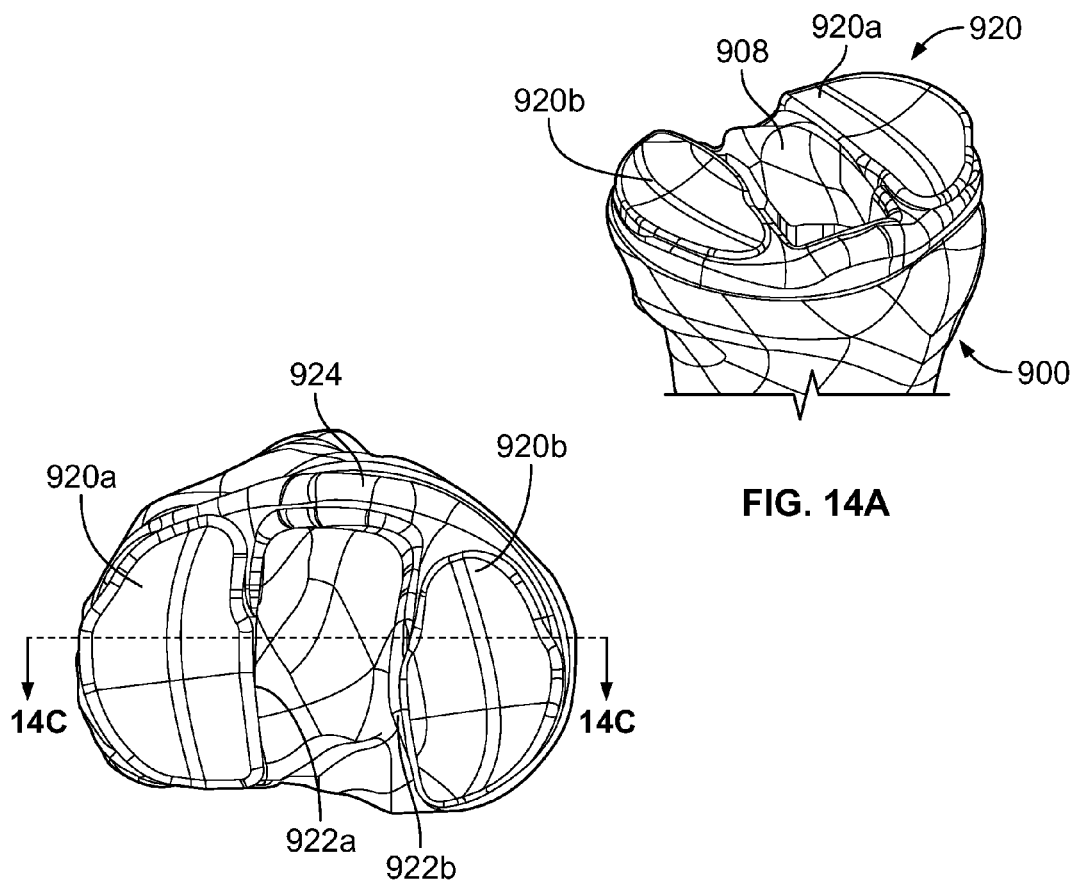
FIG. 14A
FIG. 14B
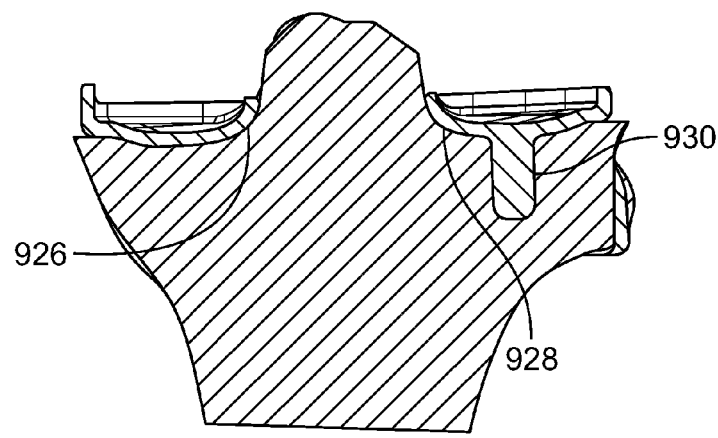
FIG. 14C

MORPHOLOGICALLY CURVED SAGITTAL WALL OF A TIBIAL IMPLANT

BACKGROUND OF THE INVENTION

Current knee arthroplasty tibial implants that retain the tibial eminence contain a straight sagittal wall portion which banks against the eminence. Typically, the sagittal wall resection of the eminence corresponding to the straight sagittal wall of an implant is made with a reciprocating saw normal to the transverse tibial resection plane. When placing an eminence-preserving implant, preferences to component placement on a cut plane include avoiding ligaments, optimizing bony coverage, avoiding deep cuts into the eminence, and permitting possible kinematic trialing feedback, for example.

However, a straight walled implant may not be the most optimal design to retain constant resection depth on both sides of the eminence and to avoid ligaments because the native eminence wall itself is not a perfectly straight line. A straight walled implant also may not provide sufficient anterior-posterior stability.

SUMMARY OF THE INVENTION

Tibial implants having a curved sagittal wall portion taking into account both general anatomic features of the proximal tibia as well as providing greater anterior-posterior stability than implants having a straight sagittal wall portion are described herein. Further, by modifying the sagittal wall of the implant itself, issues like cutting too close to the anterior cruciate ligament ("ACL") and cutting deep into the eminence to optimize placement can be avoided over large populations.

An aspect of the invention is bone preservation of the proximal tibia, namely the eminence. A consistent eminence height or equal height to final implant geometry allows for more conservation of bone than a straight cut affords. For a proposed implantation position, a curved geometry is more forgiving of ligaments and high peaks of the eminentia. Therefore, if positional changes of the implant are required to optimize the implant fit or function, there will be more positional freedom before the implant is limited by interfering with these structures.

According to one aspect of the invention, a method of designing a prosthetic implant comprises generating a virtual bone model based on image information obtained from at least one bone, determining a proposed height of the prosthetic implant at a first location on the virtual bone model, determining a proposed resection depth into the at least one bone at the first location based at least in part on the proposed height of the prosthetic implant, determining a curved resection path across a portion of the virtual bone model, the curved resection path intersecting the first location, and providing a prosthetic implant having a curved sagittal wall corresponding to the curved resection path.

In accordance with one embodiment, the curved resection path follows at least one outer surface contour of the virtual bone model. According to a further embodiment, the image information obtained from the at least one bone includes a database of knee data measurements taken from a plurality of knees. According to still further embodiment, the information from at least one bone consists of a plurality of measurements taken from a single knee.

According to one embodiment, the prosthetic implant is a tibial implant. According to a further embodiment, the tibial implant is a unicompartmental tibial implant. According to a still further embodiment, the tibial implant is a bicompartmental tibial implant.

According to one embodiment, the curved resection path substantially corresponds to the geometry of the tibial eminence. According to a further embodiment, at least a portion of the sagittal wall is defined by a rotation about a first pivot point. According to a still further embodiment, the curved resection path substantially corresponds to the geometry of the tibial eminence. According to a further embodiment, at least a first portion of the sagittal wall is defined by a rotation about a first pivot point at a first diameter, and a second portion of the sagittal wall is defined by a rotation about the first pivot point at a second diameter.

According to a further aspect of the invention, a prosthetic implant comprises a first surface for facing bone, a second surface, opposite the first surface, for facing a joint, and a sagittal wall extending between the first and second surfaces, wherein the sagittal wall traverses a non-linear path across the first and second surfaces, and wherein the non-linear path is based on the dimensions of at least one bone.

According to one embodiment, the implant is a tibial implant. According to a further embodiment, the tibial implant is a unicompartmental prosthetic implant. According to a still further implant, the prosthetic tibial implant is a bicompartmental tibial implant.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIGS. 4A-C are top, front and side views of a virtual bone model of a proximal tibia having a medial point field map demonstrating measurements from surface points along contours of the bone to a proposed resection plane.

FIGS. 6A-C are top, front and side views of a virtual bone model of a proximal tibia having a lateral point field map demonstrating measurements from surface points along contours of the bone to a proposed resection plane.

FIGS. 7A-B are top plan views and FIGS. 7C-D are lateral and medial side views of a virtual bone model of a proximal tibia illustrating proposed bone resections with a straight sagittal wall.

FIGS. 9A-C are top plan views of a virtual bone model of a proximal tibia illustrating surface contours and proposed bone resections having a curved sagittal wall.

FIG. 14A is a perspective view of a virtual bone model of a proximal tibia illustrating a bone resection and a bicompartmental tibial implant with medial and lateral components each having a curved sagittal wall.

FIG. 14B is a top plan view of the virtual bone model of the proximal tibia and bicompartmental tibial implant of FIG. 14C.

FIG. 14C is a cross-sectional view showing the bicompartmental implant engaged to the resected proximal tibia taken along line 14C-14C of FIG. 14B.

DETAILED DESCRIPTION

Figure 1:
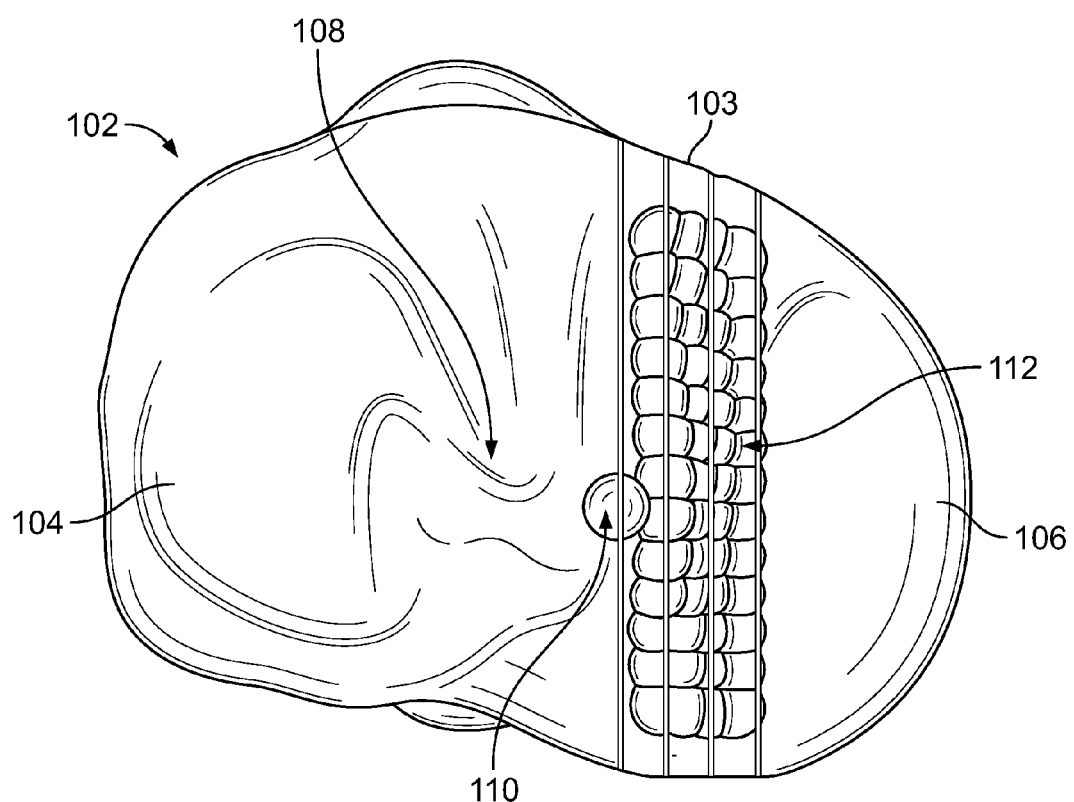
FIG. 1 is a top view of a virtual bone model of a proximal tibia with a point field map on a medial condyle thereof.

Referring to the drawings, wherein like reference numerals represent like elements, there is shown in the figures, in accordance with embodiments of the present invention, prosthetic implants and virtual bone models. FIGS. 1-4 illustrate one method of designing a prosthetic implant for fabrication having a curved sagittal wall using a virtual bone model 102. In this embodiment, the method includes obtaining or generating at least one virtual bone model 102. Bone model 102 is a bone model of a proximal tibia 103 having lateral 104 and medial 106 portions or sides. The lateral 104 and medial 106 sides are separated by a tibial eminence 108.

A height or high point 110 is identified on bone model 102 representing a location on the bone model that is the greatest linear distance away from a proposed resection depth defined by a plane 114 measured about a longitudinal axis of bone model 102. In the present embodiment, high point 110 corresponds to the high point of the medial tibial spine of bone model 102 of the proximal tibia shown. The high point 110 serves as a reference for additional points on bone model 102 to create a point field map 112. Measurement locations or points 112a, 112b, and 112c are defined as millimeter offsets from one of the medial and lateral identified spine high points 110, and as percentages of the total anterior to posterior distance at each offset plane. Measurements are made from each measurement point 112a, 112b, and 112c, for example, on point field map 112 to a point on the proposed resection plane 114. The respective measurement point 112a, 112b, and 112c and point on the proposed resection plane defining a line representing the height and/or resection depth, the line being parallel to the longitudinal axis of the bone model 102.

Figure 2:
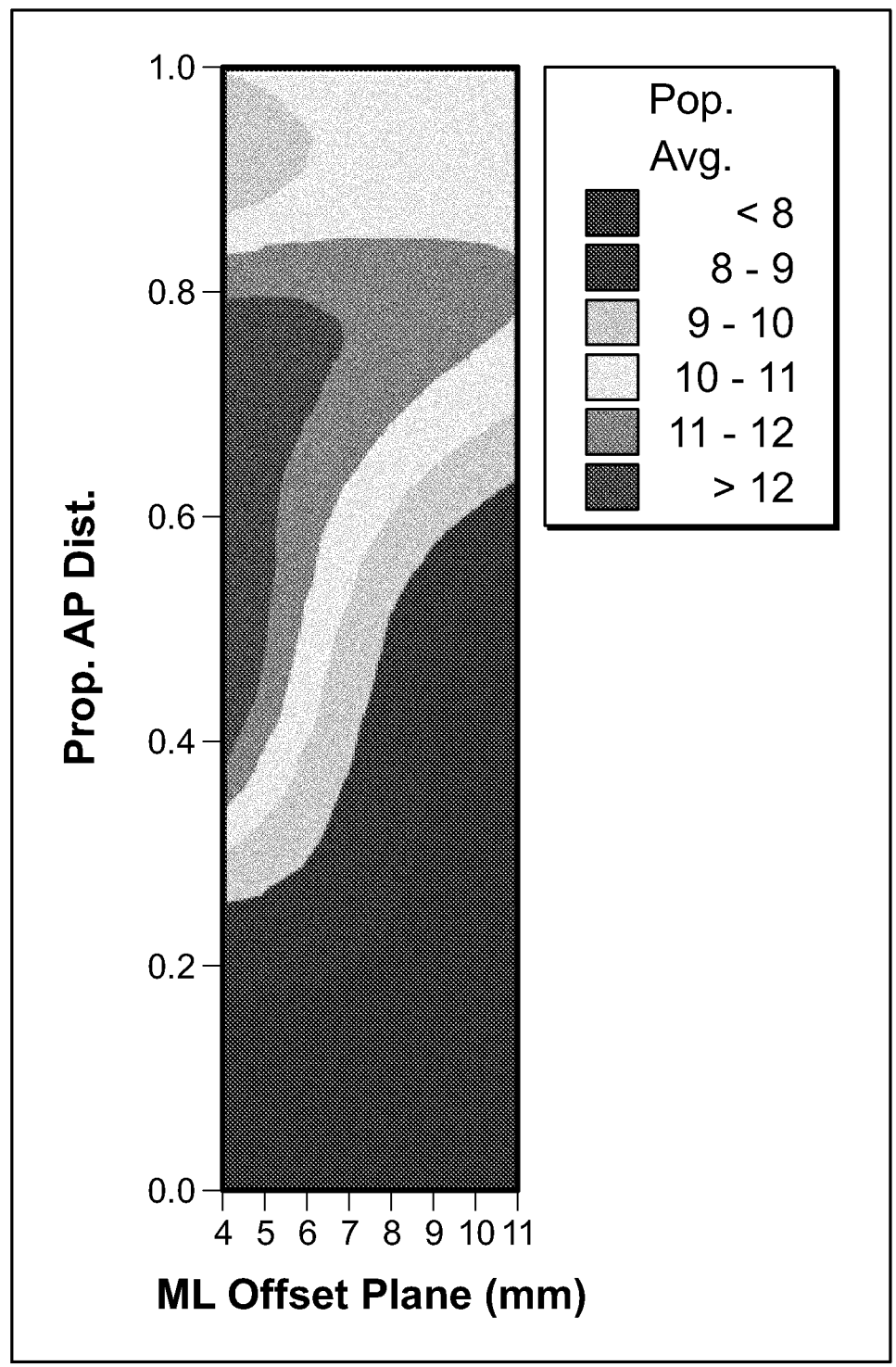
FIG. 2 is a contour plot comparing medial eminence height to resection level.
Figure 3:
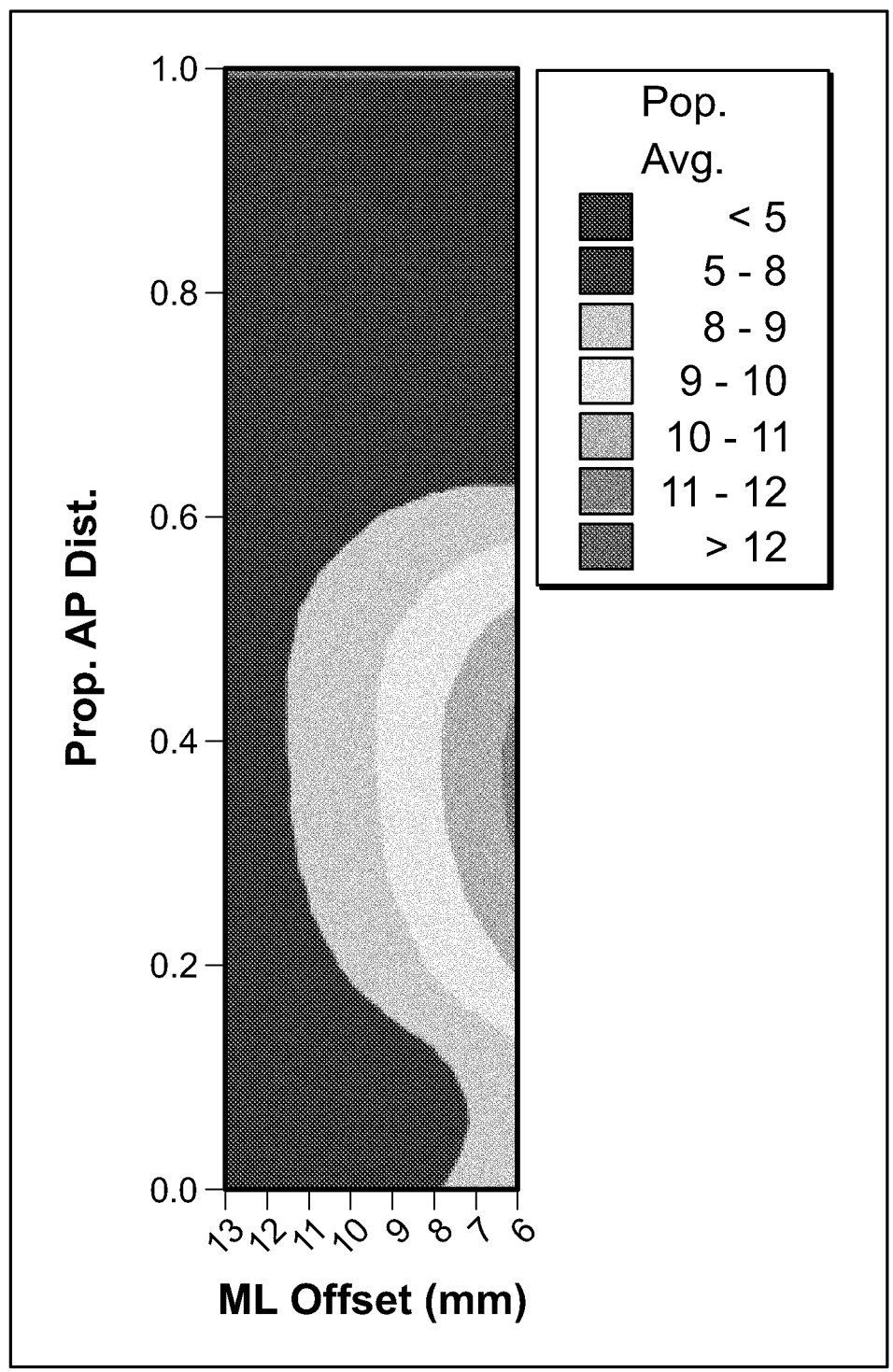
FIG. 3 is a contour plot comparing lateral eminence height to resection level.

FIGS. 2 and 3 show the results of measurements taken on over 540 tibias generated using a database including information on patient morphology such as size, shape, density, and inner and outer cortical boundaries drawn from diverse populations to represent a broad range of patients. Point field maps 112 created on the medial and lateral condyles each contain 104 measurement points to define contour lines on either side of the tibial eminence 108. Additionally, tibiae were split into multiple sizes based on their primary sizing measure such as anterior-posterior length, for example. Measurements from each size group then had a contour plot created based on its point field height measurements and variability of each measurement.

A prosthetic implant can then be designed based on the measurements taken and/or the created contour plots. In one embodiment, the prosthetic implant being designed for later fabrication is a medial tibial implant. The sagittal geometry of the tibial implant can be created to follow or mirror the contours of the virtual bone model at a proposed height, or a determined offset from the proposed height of the tibial implant. The resultant tibial implant has a sagittal wall that allows for a constant eminence height on average along its length. In one embodiment, the tibial implant can be designed to have the same height of the bone cut by both curving the cut and changing the implant height depending on region of the sagittal cut height.

If it is preferable to have the implant below the eminence, then acceptable bounding criteria can be developed, and using the variability of the normally distributed data of each height point measured, a periphery can be defined that captures the largest population of patients within the acceptable bounding criteria.

Figure 5:
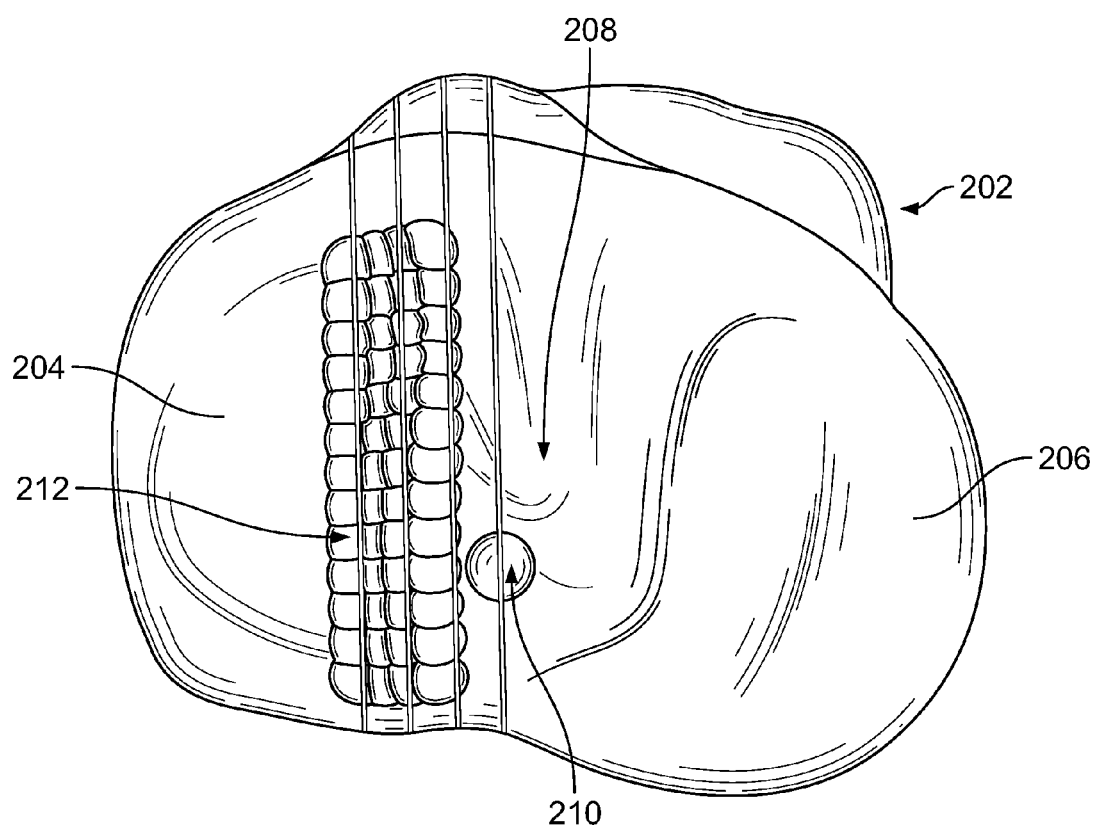
FIG. 5 is a top view of a virtual bone model of a proximal tibia having a point field map on the lateral condyle showing a high point on the virtual bone model.
Figure 8A:
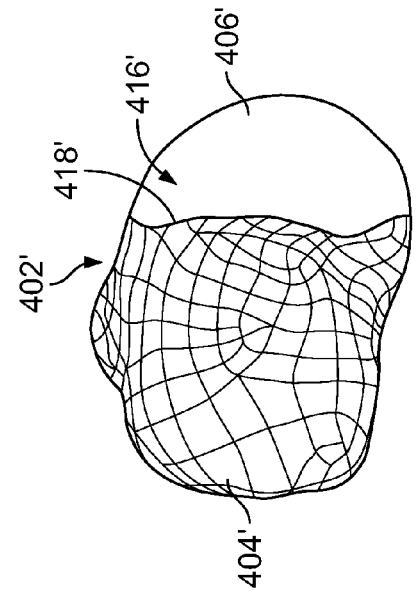
FIGS. 8A-B are top plan views and FIGS. 8C-D are lateral and medial side views of a virtual bone model of a proximal tibia illustrating proposed bone resections having a curved sagittal wall.
Figure 8B:
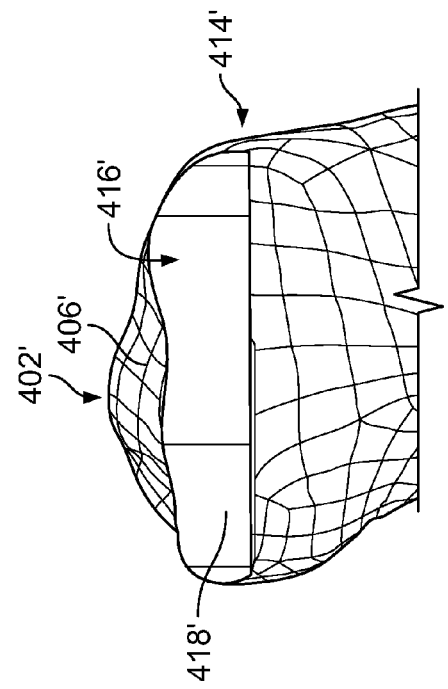
Figure 8C:
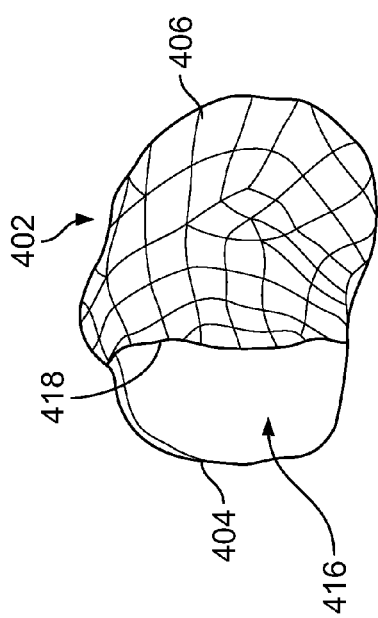
Figure 8D:
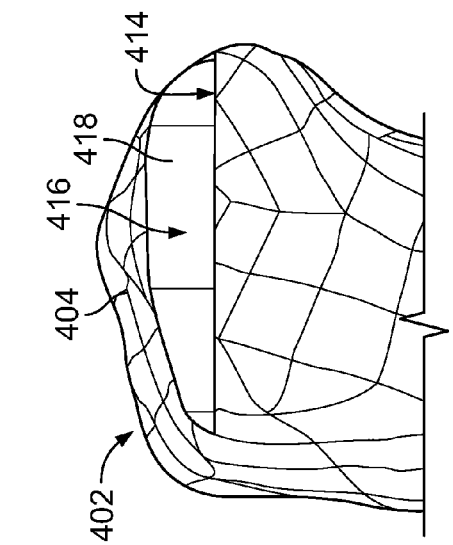
Figure 10B:
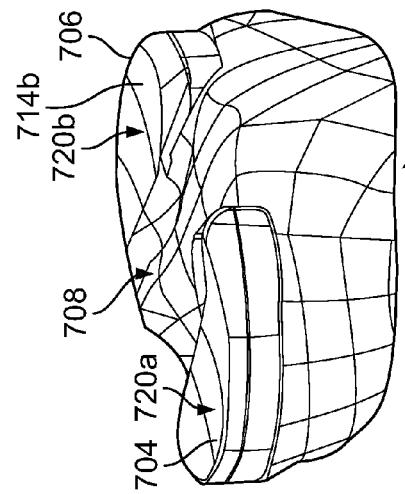
FIGS. 10A-D are perspective views of a virtual bone model of a proximal tibia illustrating bone resections with corresponding medial and lateral tibial components each having a curved sagittal wall.
Figure 10D:
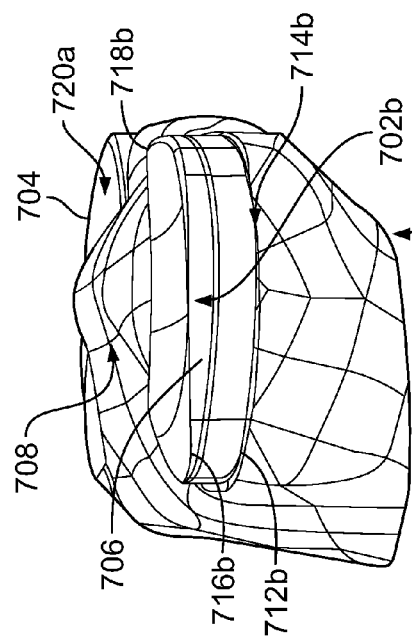
Figure 10A:
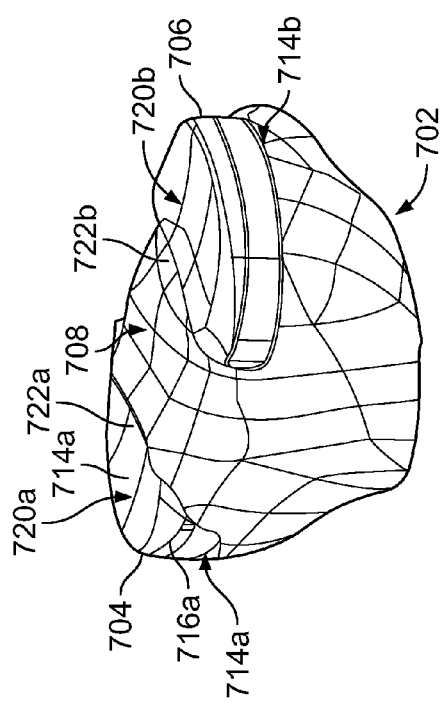
Figure 10C:
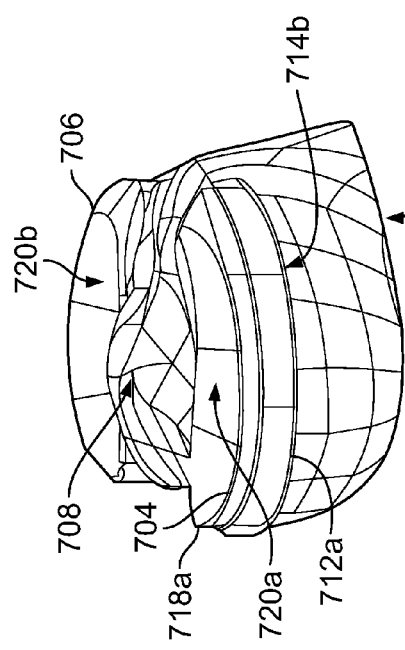
Figure 11:
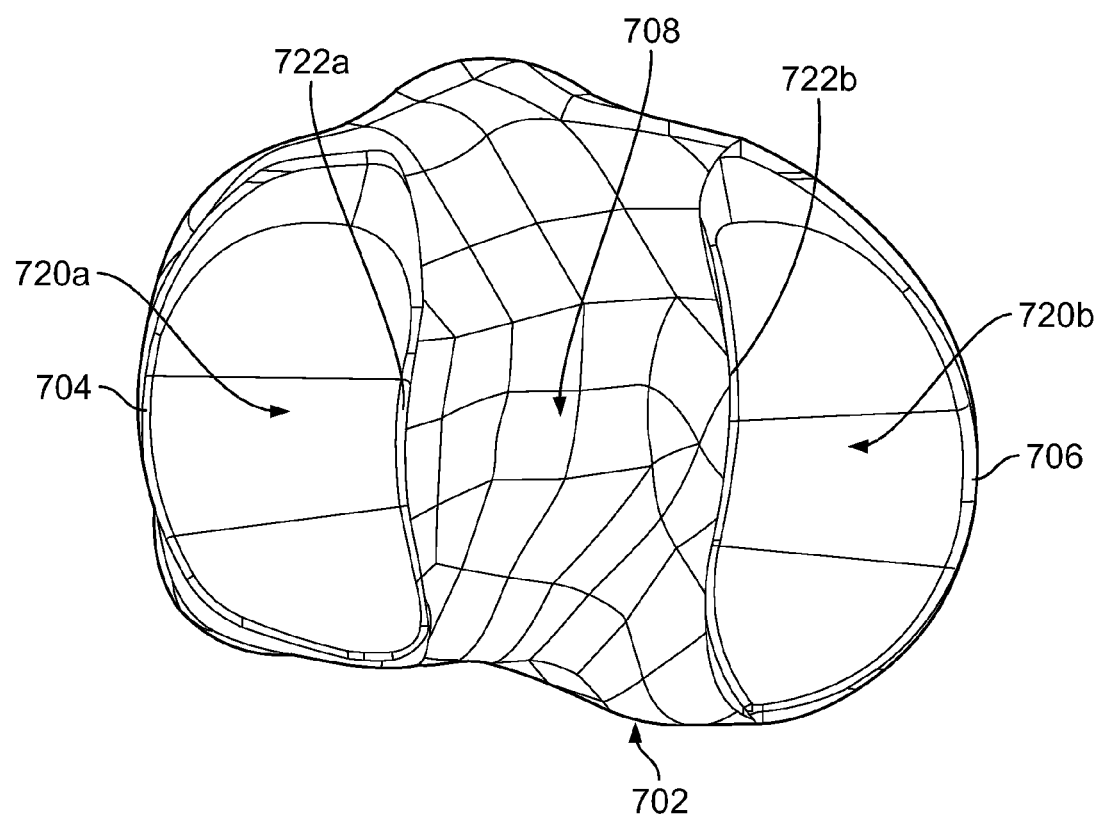
FIG. 11 is a top plan view of a virtual bone model of a proximal tibia illustrating bone resections with corresponding medial and lateral tibial components each having a curved sagittal wall.

In FIGS. 5-6, point field maps are created on the lateral portion 204 of the bone model 202. The bone model 202 is a model of a proximal tibial bone model having lateral 204 and medial 206 sides. The lateral 204 and medial 206 sides are separated by a tibial eminence 208.

One or more heights or high points 210 are identified on the surface of the bone model 202, representing a surface location that is the greatest distance away from one or more proposed depths defined by resection planes 214. The high point 210 then serves as a reference for additional measurement points on the bone model to create a point field map 212. In this example, the high point 210 corresponds to the high point of the lateral tibial spine. Measurement locations or points 212a, 212b, and 212c are defined as millimeter offsets from one of the one or more identified high points 210, and percentages of the total anterior to posterior distance at each offset plane. Measurements were made from each described point on the point field map to the proposed resection plane.

The implant sagittal geometry is then created to follow the contour plot at the implants proposed height, or an offset of the implants height for each size. The resultant tibial sagittal cuts then follow a constant eminence height on average along their length, which is mirrored in implant design.

FIGS. 7A-D illustrate different views of a bone model 302, 302' showing proposed lateral 316 and medial 316' resections having a straight sagittal wall 318, 318'. In these illustrations, bone models 302, 302' are of a proximal tibia having a lateral side 304, 304' and a medial side 306, 306', respectively. A resection plane 314, 314' defines the depth of resection into the proximal tibia that will be made. The proposed resected portion 316, 316' corresponds to an area of bone that will be removed and made available for replacement by a tibial implant. As shown best in FIGS. 7A and 7B, the sagittal wall 318, 318' defining the interface between the bone 302, 302' and the proposed resected portion 316, 316' is a linear line bisecting a proximal outer surface of bone model 302, 302', respectively.

FIGS. 8A-D illustrate different views of a bone model 402, 402' showing proposed lateral 416 and medial 416' resections having a curved sagittal wall 418, 418', wherein the curvature is based, in part, on the tibial eminence geometry. In the embodiments shown, bone model 402, 402' is a proximal tibia having a lateral side 404, 404' and a medial side 406, 406', respectively. A resection plane 414, 414' defines the depth of resection into the proximal tibia that will be made. A proposed resected portion 416, 416' corresponds to an area of bone that will be removed and made available for replacement by a tibial implant.

Moreover, the proposed resection level 414, 414' is preferably a planar resection level having an orientation about a longitudinal axis of the bone that is determined based on desired component placement in order to achieve planned internal-external rotation, varus-valgus angle, and flexion-extension axis of the knee joint once the component is positioned thereon. As shown best in FIGS. 8A and 8B, the sagittal wall 418, 418' defining the interface between the bone 402, 402' and the proposed resection portion 416, 416' is curved and/or non-linear. The curvature in this example is based at least in part on the outer contour of medial and lateral portions of the tibial eminence. The curved path of the sagittal wall 418, 418' substantially follows a surface contour representing a constant bone height as measured from resection plane 414, 414'.

FIGS. 9A-C illustrate surface contour plots along a bone model 502 having proposed resection areas 516, 516'. A surface contour plot corresponds to bone model 502 that is a proximal tibia having a lateral side 504 and a medial side 506. The lateral 504 and medial 506 sides are separated by a tibial eminence 508. The contour plot identifies a resection portion 516, 516' having a sagittal wall 518, 518' that is curved. The curved sagittal wall 518, 518' substantially follows a constant tibial height as measured from a proposed resection level.

In FIGS. 10A-D and 11, a proximal tibia 702 is shown having resected areas on both lateral 704 and medial 706 sides, i.e., on either side of tibial eminence 708. Tibial implant portions 720a and 720b have curved sagittal walls 722a and 722b, respectively, corresponding to the height contours of the adjacent bone of the proximal tibia 702 such that there is a substantially smooth transition between native bone of the tibial eminence and an outer or articular surface of tibial implant portions 720a and 720b.

In the embodiment shown, the tibial implant is a bicompartmental tibial implant including both lateral 720a and medial 720b implant portions. In other embodiments, the tibial implant may be a unicompartmental or unicondylar implant in which only one of lateral 720a and medial 720b implant portions is utilized. The lateral portion 720a corresponds to the lateral side 704 of the tibia, and the medial portion 720b corresponds to the medial side 706 of the tibia. Each portion 720a and 720b has a respective bone contacting surface 712a and 712b, an articular surface 714a and 714b, and a sagittal wall 722a and 722b extending between the bone contacting and articular surfaces. The sagittal wall 722a and 722b traverses a non-linear path from an anterior portion 716a, 716b to a posterior portion 718a, 718b of the implant portions 720a, 720b. Sagittal wall 722a and 722b have curvature corresponding to the contours of the tibial eminence 708 such that the height of the resected bone interfacing with the sagittal wall of the implant portions 720a and 720b remains constant with respect to the resection level 714a and 714b, respectively.

Figure 12:
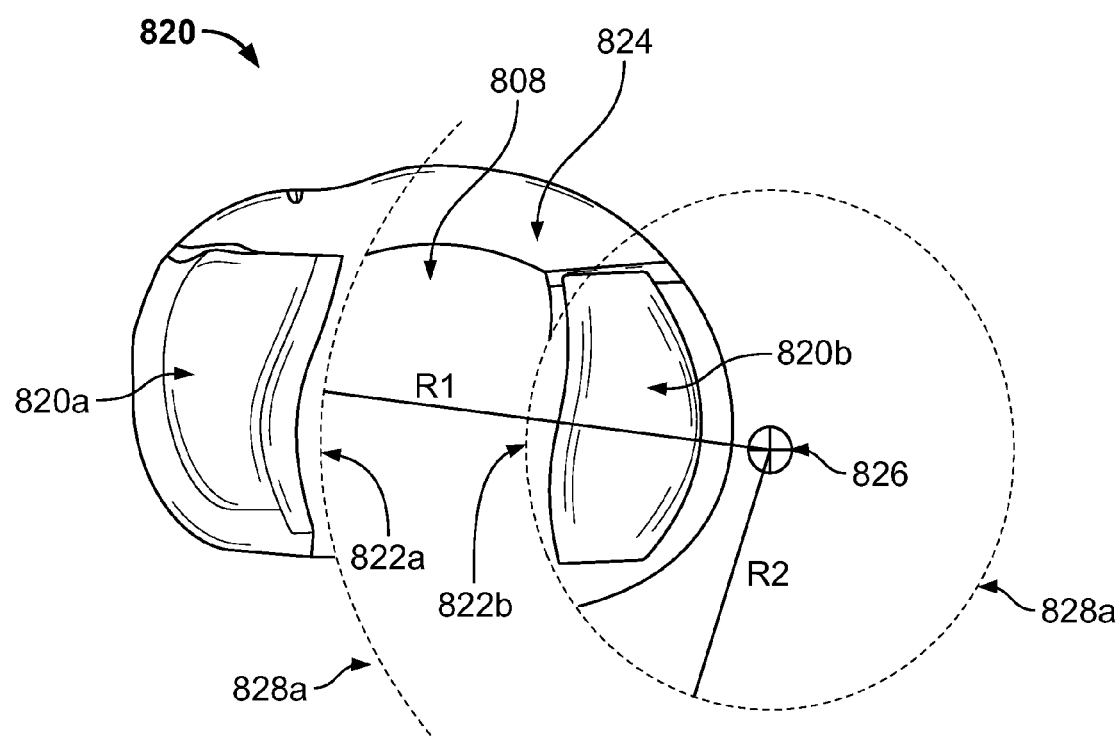
FIG. 12 is a top view of a bicompartmental tibial implant having medial and lateral portions each having a curved sagittal wall as to allow a rotational or helical insertion path about a pivot point.
Figure 13:
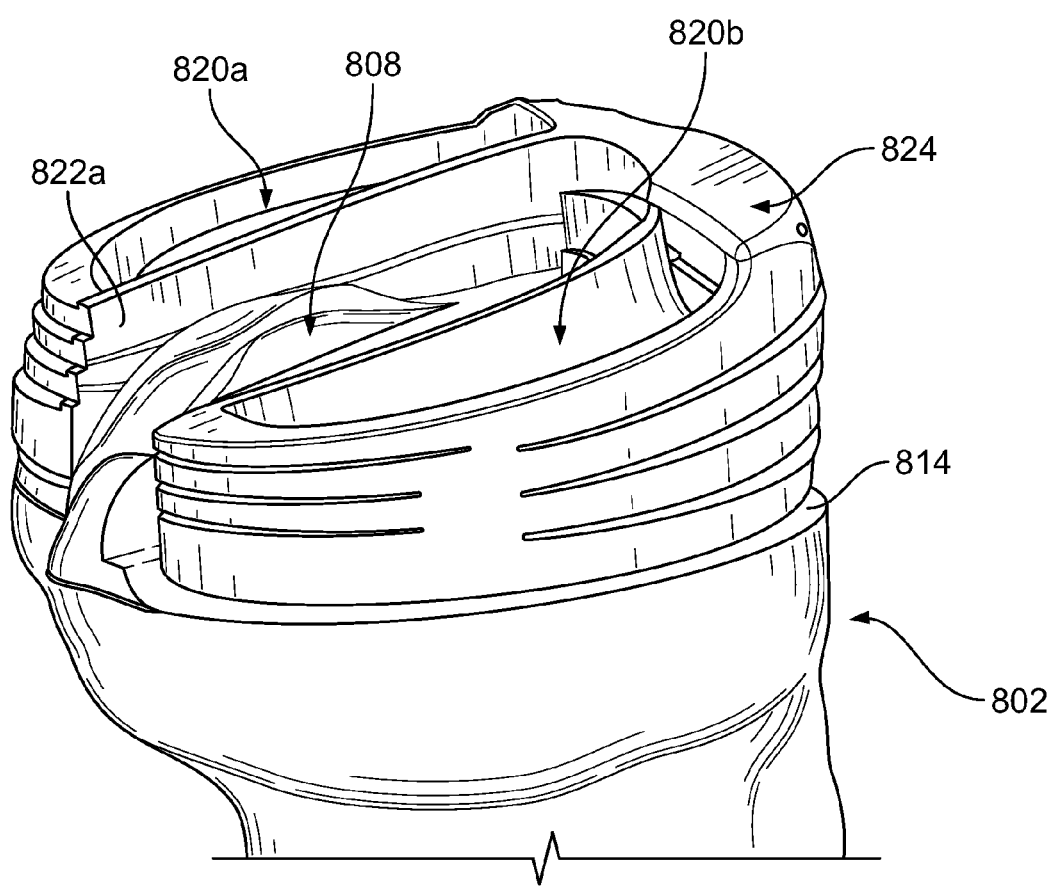
FIG. 13 is a perspective view of a virtual bone model of a proximal tibia illustrating a bone resection and a plurality of stackable bicompartmental tibial implants each with medial and lateral portions each having a curved sagittal wall.

In a further embodiment, an implant may have an eminence geometry further defined as a rotation about a pivot point as described, for example, in U.S. Pat. Pub. No. 2012/0330429, titled "Prosthetic Implant and Method of Implantation," the entirety of which is hereby incorporated by reference herein. As illustrated in FIGS. 12-13, a prosthetic implant 820 has a lateral portion 820a and a medial portion 820b. The implant 820 further has a connecting portion 824 connecting the lateral 820a and medial 820b portions, such that the implant 820 has an open central portion 808 for, as an example, circumscribing a tibial eminence.

Additionally, the sagittal walls 822a and 822b of the lateral 820a and medial 820b portions have a curved geometry such that the walls 822a and 822b are swept about a single pivot point 826. In other words, the geometry of the sagittal walls 822a and 822b substantially follow curvatures 828a and 828b that circumscribe a common pivot point 826 such that the curvatures 828a and 828b are portions of a circumference of concentric circles about pivot point 826. Each curvature 828a and 828b has a respective radius R1 and R2 with pivot point 826. The implant 820 is therefore inserted into place at the proposed resection level 814 in a rotational motion, which once fully positioned, increases the stability of implant 820 with respect the resected proximal tibia. Further, the implant could also be tapered towards the eminence, which may decrease the chance for eminence avulsion, aid in decreasing component micromotion, and ease the insertion process. An implant design with the features described should be more resistant to physiological loading than current designs with straight walls contacting the eminence.

FIG. 14A-C show a bicompartmental tibial implant 920 engaged to a resected virtual bone model 900 of a proximal tibia. The bicompartmental tibial implant 920 has lateral 920a and medial 920b component portions each having a curved sagittal wall. The implant 920 further has a connecting portion 924 connecting the lateral 920a and medial 920b portions, such that the implant 920 has an open central portion for, as an example, circumscribing a tibial eminence 908.

Additionally, the sagittal walls 922a and 922b of the lateral 920a and medial 920b portions have a curved geometry such that the walls 922a and 922b may be swept about a single pivot point. Further, implant 920 is tapered 926, 928 towards eminence 908, as shown for example in FIG. 14C, which may decrease the chance for eminence avulsion, aid in decreasing component micromotion, and ease the insertion process. Here, an interference fit between a fixation post 930 of tibial implant 920 acts to push eminence 908 down an provide a secure engagement between tapered 926, 928 sections of tibial implant 920 and eminence 908.

The methods of designing the implants described herein can be applied to other joints of the body, such as the hip, elbow, shoulder, wrist and ankle, for example. Effective resection depth and natural bony contours of these joints can be taken into account in designing such implants in order to stabilize the implants with respect to resected bone in order to restore joint motion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A method of manufacturing a prosthetic implant comprising:
   generating a virtual bone model based on image information obtained from at least one bone;
   determining a proposed height of the prosthetic implant at a first location on the virtual bone model;

determining a proposed resection depth into the at least one bone at the first location based at least in part on the proposed height of the prosthetic implant;

determining an at least partially curved resection path across a portion of the virtual bone model, the curved resection path intersecting the first location and following at least one outer surface contour on the virtual bone model such that there is a substantially smooth transition between the virtual bone model and the curved resection path; and fabricating a prosthetic implant having a curved sagittal wall corresponding to the curved resection path.

2. The method of claim 1, wherein the image information obtained from the at least one bone includes a database of knee data measurements taken from a plurality of knees.

3. The method of claim 1, wherein the information from the at least one bone consists of a plurality of measurements taken from a single knee.

4. The method of claim 1, wherein the prosthetic implant is a tibial implant.

5. The method of claim 4, wherein the tibial implant is a unicompartmental tibial implant.

6. The method of claim 4, wherein the tibial implant is a bicompartmental tibial implant.

7. The method of claim 1, wherein the virtual bone model comprises a tibial eminence.

8. The method of claim 7, wherein the at least partially curved resection path corresponds to at least one outer surface contour of the tibial eminence.

9. The method of claim 1, wherein at least a portion of the curved sagittal wall of the prosthetic implant is defined by a rotation of the prosthetic implant about a first pivot point.

10. The method of claim 1, wherein the prosthetic implant has a first curved sagittal wall and a second curved sagittal wall at least partially defined by a rotation of the prosthetic implant about a pivot point.

11. The method of claim 10, wherein the rotation of the prosthetic implant about the pivot point creates a first radius between the first sagittal wall and the pivot point and a second radius between the second sagittal wall and the pivot point.

12. The method of claim 1, wherein the proposed resection depth into the at least one bone is at least partially defined by a resection plane on the virtual bone model, the resection depth at the first location being based at least in part on a linear distance from a point on an outer surface of the virtual bone model to the resection plane.

13. A method of manufacturing a prosthetic implant comprising:

generating a virtual bone model based on image information obtained from at least one bone;

determining a resection plane on the virtual bone model;

determining an at least partially curved resection path across a sagittal plane of the virtual bone model, the curved resection path following at least one outer surface contour on the virtual bone model such that there is a substantially smooth transition between the virtual bone model and the curved resection path; and fabricating the prosthetic implant having a curved sagittal wall corresponding to the at least partially curved resection path across the sagittal plane of the virtual bone model, wherein a height of the curved sagittal wall corresponds to a linear distance from the at least partially curved resection path to the resection plane on the virtual bone model.

14. The method of claim 13, wherein the at least partially curved resection path is determined by selecting a plurality of points on an outer surface of the virtual bone model.

15. The method of claim 13, wherein the virtual bone model comprises a tibial eminence, and the at least partially curved resection path corresponds to at least one outer surface contour of the tibial eminence.

16. The method of claim 13, wherein at least a portion of the curved sagittal wall of the prosthetic implant is defined by a rotation of the prosthetic implant about a first pivot point.

17. The method of claim 16, wherein the rotation of the prosthetic implant about the pivot point creates a first radius between the first sagittal wall and the pivot point and a second radius between the second sagittal wall and the pivot point.

18. The method of claim 13, wherein the prosthetic implant has a first curved sagittal wall and a second curved sagittal wall at least partially defined by a rotation of the prosthetic implant about a pivot point.

19. The method of claim 13, wherein the proposed resection depth into the at least one bone is at least partially defined by a resection plane on the virtual bone model, the resection depth at the first location being based at least in part on a linear distance from a point on an outer surface of the virtual bone model to the resection plane.

* * * * *